(12) United States Patent
Peuker et al.

(10) Patent No.: US 8,794,433 B2
(45) Date of Patent: Aug. 5, 2014

(54) PACKAGE ASSEMBLY FOR DENTAL SUBSTANCES

(75) Inventors: Marc Peuker, Schondorf (DE); Arno Hohmann, Munich (DE); Dieter Poschmann, Starnberg (DE); Michael Knee, Peissenberg (DE)

(73) Assignee: 3M Innovative Properties Company, Saint Paul, MN (US)

( * ) Notice: Subject to any disclaimer, the term of this patent is extended or adjusted under 35 U.S.C. 154(b) by 1301 days.

(21) Appl. No.: 10/598,994

(22) PCT Filed: Mar. 18, 2005

(86) PCT No.: PCT/EP2005/002935
§ 371 (c)(1),
(2), (4) Date: Sep. 18, 2006

(87) PCT Pub. No.: WO2005/089667
PCT Pub. Date: Sep. 29, 2005

(65) Prior Publication Data
US 2007/0158350 A1    Jul. 12, 2007

(30) Foreign Application Priority Data
Mar. 18, 2004 (EP) ..................................... 04006543

(51) Int. Cl.
*A61B 19/02* (2006.01)
(52) U.S. Cl.
USPC ............................... 206/63.5; 53/471; 53/492

(58) Field of Classification Search
USPC ...................... 206/368, 63.5, 38, 37; 202/368;
220/281, 282, 260; 215/301, 305, 295;
433/49, 57, 61, 89, 115, 163; 224/217;
53/492, 471
See application file for complete search history.

(56) References Cited

U.S. PATENT DOCUMENTS

| | | | | |
|---|---|---|---|---|
| 2,399,834 A | | 5/1946 | Seltzer ............................. 32/40 |
| 4,873,193 A | * | 10/1989 | Jensen et al. ................... 436/176 |
| 4,991,759 A | * | 2/1991 | Scharf ............................ 224/217 |
| 5,048,731 A | * | 9/1991 | Moreschini ................... 433/163 |
| 5,204,130 A | * | 4/1993 | McDevitt et al. ............. 426/115 |
| 5,249,963 A | * | 10/1993 | McGarrigle ................... 433/163 |

(Continued)

FOREIGN PATENT DOCUMENTS

DE           476 178           5/1929

*Primary Examiner* — Jacob K Ackun
*Assistant Examiner* — Jenine Pagan
(74) *Attorney, Agent, or Firm* — Qiang Han; 3M Innovative Properties Company

(57) ABSTRACT

The present invention is directed to a package assembly for placing it on a surface and for storing and/or delivering substances, preferably dental substances, comprising: at least one container with at least one base and at least one lid; and at least one hinge connecting the base and the lid; wherein the base and the lid comprise at least a first and second lever; the first and second levers are provided at the container essentially on the side of the hinge and; a projection of the first lever onto the surface and the second lever extend with their free ends essentially in a direction away from the hinge; and wherein the container can be opened or the lid can be removed from the base by moving the ends of the first and second lever towards to each other. The invention is further directed to a method for providing dental substances, a kit with an assembly, as well as the use of an assembly and a method for storing and/or delivering dental substances.

35 Claims, 10 Drawing Sheets

(56) References Cited

U.S. PATENT DOCUMENTS

| | | | |
|---|---|---|---|
| 5,368,482 A * | 11/1994 | Johnsen et al. | 433/163 |
| 5,377,823 A * | 1/1995 | Steen et al. | 206/63.5 |
| 5,660,273 A * | 8/1997 | Discko, Jr. | 206/229 |
| 5,732,862 A * | 3/1998 | Bull | 224/217 |
| 5,938,018 A * | 8/1999 | Keaveney et al. | 206/261 |
| 5,976,469 A * | 11/1999 | Davis | 422/102 |
| 6,257,888 B1 * | 7/2001 | Barham | 433/163 |
| 6,343,695 B1 * | 2/2002 | Petrick et al. | 206/534 |
| 2005/0061815 A1 * | 3/2005 | Wong | 220/281 |

* cited by examiner

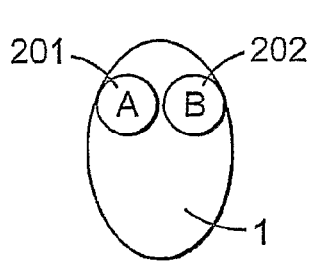
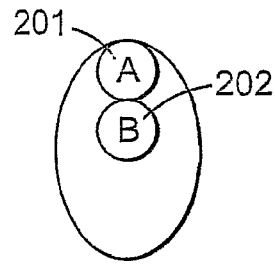
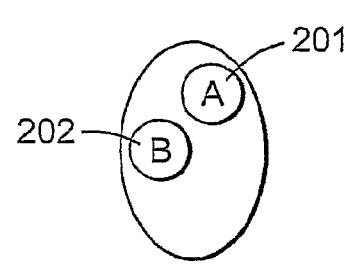
FIG. 10a    FIG. 10b    FIG. 10c
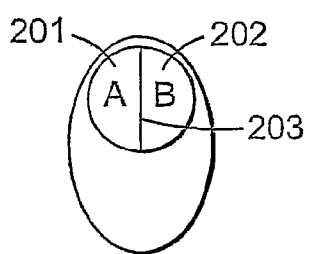
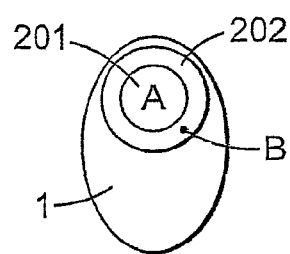
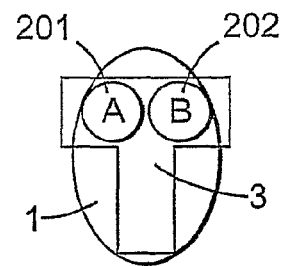
FIG. 10d    FIG. 10e    FIG. 11
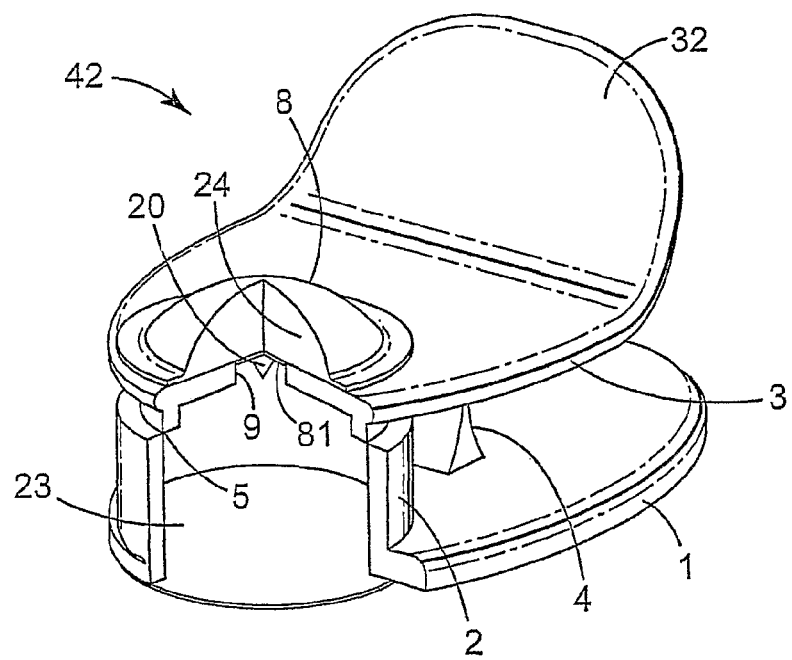
FIG. 12

PACKAGE ASSEMBLY FOR DENTAL SUBSTANCES

CROSS REFERENCE TO RELATED APPLICATIONS

This application claims priority from European Application No. 04006543.5, filed Mar. 18, 2004, the disclosure of which is incorporated by reference in its entirety herein.

The present invention relates to a package assembly for storing and delivering substances, preferably dental substances. More particularly, the present invention relates to a package assembly, which can be opened and closed "single-handedly" by an operator.

In the dental field in particular, it is often necessary to perform a large number of manual operations in succession and in a coordinated manner. To fill a cavity of a tooth, for example with a filling, the primers and bonding agents are usually packed in individual bottles in liquid form and the filling material is present as a highly viscous material in screw-cap tubes or computes. Furthermore, containers, which allow two substances to be mixed to form a single composite product, are often used in dentistry and medicine, to keep two reagents separate until they are to be used.

In many cases the dentist has only one free hand to use a dental instrument and at the same time dispense a substance and to open or reclose the package from which the substance is to be delivered. To facilitate the treatment procedure, it is highly desirable for the dentist to use the instrument to dispense the substance with one hand and avoid using a second hand to handle the package (e.g., opening, dispensing, closing).

It would be desirable to provide a device or package assembly, which can be opened and reclosed easily with one hand by an operator. Furthermore, it would be desirable to provide a device which can separately store a plurality of different substances or components, which can be mixed in the device and dispensed by using easy "one-hand" operations.

There is a particular need for a device which can store individual components or substances separately and safely, e.g., from air and light exposure or from premature exposure to each other, in a single package assembly and be able to mix them therein by an easy "one-hand" action.

This is achieved by a device and by a method for using the device, as described in the claims.

The package assembly of the present invention may be pre-filled with the desired substance(s), in particular dental substances, and it may be disposable. The substance(s) within the package assembly may be encapsulated by the package assembly to provide good stability. A preferred embodiment of the assembly is reclosable.

The package assembly can be opened prior to dispensing the substance(s) within, by using a simple "activation", which can preferably be carried out with only one hand. After opening the package assembly, it can be left on the dentist's tray or any other place while the substance is dispensed, or the substance can be dispensed single handedly while the dentist holds an instrument in the same hand.

The term "container means" can be any kind of container having at least one base and at least one lid which can hold liquid, paste, powder or rigid substance(s) such that the substance(s) are retained therein. The container means may be liquid and/or gas tight to maintain the substance(s) in an uncontaminated or sterile condition, it is not required for the invention and the desirability of such feature will depend on the intended use. Moreover, this term can embrace a containers with a single compartment or multiple compartments within a common or divided housing.

In the following the term "hinge means" embraces any integral or separate device or arrangement which allows movement of the lid and/or base of the container means such that the container means can be opened and filled or its contents can be expelled or released at least in part. Preferably, the hinge means is a device or an arrangement that allows the lid or an articulation to be pivoted away from the base. Any joint, like a swivel joint, or preferably a living or film hinge or an articulation or link can be employed, but devices allowing more complex movement like a knee-lever can also be used.

The term "fixation means" used in the present application means a mechanism which allows a releasable fixation of the lid lever and the base lever. Preferably one lever comprises a protrusion for engagement with a recess in the other lever, like a snap mechanism, clip mechanism, snap fit or the like. Other mechanisms for a releasable engaging of the two levers may be provided by adhesives, pressure sensitive adhesives, hook and loop fastener, or the like.

The present invention is additionally directed to the following embodiments:

A package assembly for storing and/or delivering substances, preferably dental substances, comprising:
 a) at least one container with at least one base and at least one lid; and
 b) at least one hinge connecting the base and the lid;
 c) wherein the base and the lid comprise at least a first and second lever;
 d) the first and second levers are provided at the container essentially on the side of the hinge and,
 e) a projection of the first lever onto the surface and the second lever extend with their free ends essentially in a direction away from the hinge;
 f) and wherein the container can be opened or the lid can be removed from the base by moving the ends of the first and second lever relative or towards to each other.

It is further preferred that the hinge is provided between the first and second lever.

Preferably the container comprises a first end next to the base and a second end next to the lid, which is adapted for an air tight closing of the container at the second end.

It is moreover preferred that the end of the second lever is bent in a direction away from the first lever.

Even further preferred is that the base and the lid are molded, preferably injection molded.

Even further preferred is that the base, the lid and the hinge are integrally molded.

Even further preferred is that the base, the lid are molded as one piece with a weakened line for later separating the lid from the base.

Even further preferred is that the hinge is a living hinge or film hinge.

Even further preferred is that the base and/or the lid are manufactured with an opening for filling the container after manufacturing it and for sealing with a sealing.

Even further preferred is that the first and/or second lever comprise(s) a fixation for attaching the second lever to the first lever and to ensure that the lid stays open after having been opened.

Even further preferred is that the package is designed for two- or multi-component substances.

Even further preferred is that the container comprises at least two containers.

Even further preferred is that the at least two containers are arranged adjacent to each other.

Even further preferred is that the at least two containers are provided separately with independent openings.

Even further preferred is that the at least two containers comprise one common lid.

Even further preferred is that the common lid is T-shaped, in case the two containers are arranged side by side, and allows a sequentially activation of the containers.

Even further preferred is that there is provided an area adapted for swabbing a brush or a mixing cavity for mixing components with a brush.

Even further preferred is that the mixing cavity is part of the container and is re-closable by the lid.

Even further preferred is that the lid comprises a second container adapted for storing a substance.

Even further preferred is that the second container and/or the lid comprises a bore adapted for connecting the capacity of the container with the capacity of the second container of the lid for dispensing the substance into the container.

Even further preferred is that the bore is sealed by a base foil of a sachet.

Even further preferred is that upon activation the base foil of the sachet will rupture at the bore for dispensing the additional substance into the container.

Moreover the invention is directed to a method for providing dental substances, comprising the steps of:
a) providing a package assembly according to any of the previous claims,
b) opening the initial closed package assembly by pressing the two lever together, and
c) taking the substance out of the container.

It is further preferred that before step b) the further step is provided:
a1) pressing the lid in the direction of the container for breaking the seal.

Even further preferred is that after step c) the further step is provided:
d) closing the container by pressing the lid onto the container.

Even further preferred is that the assembly according to the present invention further comprises at least one of the following materials: dental primers; bondings; etching gel/liquids; filling materials, such as composites, resign modified glass ionomer cements; temporary filling material; varnishes; glue, such as cyanoacrylate; pharmaceuticals, such as liquids, gels, pastes; varnishes; nail polish; touch up paints; cosmetics, such as lip gloss, a substance for the treatment or prevention or identification of caries; a substance for the prevention or identification or removal of plaque; a substance for root canal treatment; a substance for the removal of carious or decayed or infected dentine or enamel and/or a substance for the removal of denaturated dentine.

Even further preferred is that there is a kit with an assembly according to the present invention further comprising at least one of the following members: dental instruments, such as excavators, in particular disposable dental instruments; brushes, particularly of different sizes and hardnesses; disposable cartridges so that the system can be used as a refillable system; gloves and/or at least any one of the materials mentioned above; and/or bonding and/or etching agent/gel.

The container comprises a first end, adjacent to the base and a second end, located adjacent to the lid. Preferably, the lid is adapted to provide an air-tight closing or seal at the interface of the lid and the second end of the container. For easy, "one-hand" or "one-finger" opening and closing of the assembly, the end of the lever can be pushed and can preferably bent away from the base.

The preferred material for the base and lid comprises plastic, which provides fast, easy and cheap production through use of conventional molding techniques. In a preferred embodiment, the base, the lid and the hinge are integrally molded, which can be done in a one-shot molding technique. For such assemblies, it may be advantageous to mold the container with one opening, e.g. at the first end or at the second end.

Preferably the package assembly is molded such that the container comprises the opening at the first end adjacent to the base. This is advantageous and makes it possible to mold the second end of the container and the lid integrally. The interface between the second end of the container and the lid may form a breakable seal. According to another embodiment, the package assembly is molded with a closed container at the first end, i.e. adjacent to the base. Preferably the integrally molded interface between the second end of the container and the lid forms a breakable seal. An opening for filling the container may be provided in the lid above the container. The one opening, which is according to the above described embodiments adjacent to the first or second end can be sealed after the container was filled with the substance(s).

According to another embodiment, for example when the container is molded with the base integrally and the lid is molded separately, the container may comprise either two openings or only one opening. In case of two openings, the first opening is sealed before a substance is filled into the container and the other opening is sealed subsequent on filling. The sealing system preferably comprises a foil and/or a plug and/or part of the base or lid. The opening for filling is alternatively arranged within the lid or in the base whereas the plug is preferably used for sealing the lid site opening. For sealing the base site bore a foil is preferred whereas the foil can cover the whole bottom surface of the base or part of it.

Before opening, the container comprises preferably at least one dental substance and the container is closed at the second end by the lid wherein the interface between said lid and said second end is sealed with a breakable seal. In a preferred embodiment of the present invention, the breakable seal is already produced during molding. According to other preferred embodiments, like separate molding the container and the lid, the breakable seal can subsequently applied at the interface between the container and the lid. The breakable seal preferably provides besides an airtight sealing also a tamper-evident resistance which ensures an intact and new unused package assembly. This can preferably be achieved by using a foil which is sealed upon the container. The foil is pierced or punched by a spike or cutting edge respectively. Within the first embodiment (punching of the foil) the foil is also attached to the lid to ensure the foil is removed from the container when the package is opened and the lid stays close during transport of the package. Alternatively the foil can have a breaking line which facilitates easy rupturing during activation of the package.

To facilitate easy breaking of the breakable seal it is possible to "artificially" generate a joint line. This can be made by creating two gates in the mold, the first gate located at the lid and second at the base. The locations of the gate are chosen in a manner that the plastic materials from both gates exactly meet at the breakable seal during molding. As in the area of the breakable seal the wall is very thin an accurate generation of a joint line is facilitated. A second method to generate a breakable seal is to "overheat" the material partially or in total during molding. Latter method is easy to make by using melt temperatures for the plastic near to the upper allowed limit (or even above) thus making the plastic more brittle. The brittleness can be controlled in a way that remaining strength of the material is sufficient in areas of thicker walls. Partially overheating of the material can be made by including heating means into the mold next to the breakable seal.

For easy handling, the base of the package assembly can be provided with an adherent means to fix the package assembly to a work surface. For example, the bottom surface of the base can comprise a non-skidding and/or sticky layer which can permanently or temporarily fix the package assembly to the work surface. For example, adhesive tapes, magnets, suction cups, adhesive coatings, reclosable fasteners, and elastomeric materials can be employed for this purpose. Microreplicated films or a microreplicated surface on base can also be used. A layer or area of soft elastomeric material, can easily be provided at the circumference of the base or as a layer on the bottom surface of the base by two shot injection molding process.

To ensure that the lid stays open after opening the assembly, a fixation means or system may be provided to attach the second lever to the base. The fixation means or system comprises, for example, a recess at one lever and a protrusion at the other lever, for preferably releasingly engaging the protrusion with the recess. Another embodiment for a fixation means or system comprises fork like webs at one lever and a clips at the other lever for preferably releasingly engaging the counterpart. A further embodiment for a fixation means or system comprises an engaging means at the first and/or second lever for engaging with an edge of one of the lever. Still another embodiment comprises sticky glue or pressure sensitive adhesive for attaching the first and second lever together.

To avoid substances to remain at the lid after opening the package, the part of the lid facing the inner side of the container may comprise a low energy surface or a so called "Lotus-Effect" surface. In a preferred embodiment, this surface is microstructured and manufactured by injection molding. Alternatively fluoropolymers, like polytetrafluoroethylene, may be used as fillers for the plastic material, as two-component injection molded parts or as surface coatings or combinations hereof. Also nanoclays may be used to create low energy surfaces, increased barrier properties and/or increased brittleness to facilitate breaking of breaking zones.

As an option the container and the lid (all parts of the package getting in contact with the substances) may comprise low energy surfaces as described in order to facilitate complete emptying.

If the dental treatment is made via a brush the package may already comprise a standard disposable brush, which may be attached to the package assembly via a snap lock. In some embodiments, there may be one or more dental application tools provided with the package assembly. The tools may be of the group of swab, dental hook and probe, dental carver, pick, scraper, spatula, teasing needle, curette, Mall probe and Huber probe or any other dental tool for mixing and dispensing substances.

In some embodiments of the invention, the container comprises two or more compartments, which are arranged adjacent to each other or one may be located inside of the other. The compartments may be provided a common lid or each compartment may have a separate lid. Alternatively, separate compartments may be provided with a common lid or with separate lids. In the embodiment of a common lid, the lid may be T-shaped and cover two compartments arranged side-by-side such that opening the lid allows a sequentially activation of the containers.

A further embodiment of the package assembly comprises a lid with a flexible container, like a foil sachet, adapted for storing a substance, such that when the package assembly is in the closed position, the flexible container on the lid is adjacent to the container mounted on the base and can be activated, e.g., by piercing or pushing the container of the lid, the foil of sachet will rupture to dispense its content into the adjacent container. This embodiment is preferred if the foil of sachet contains a liquid component. In one such embodiment, the lid comprises a bore which provides the side wall of the flexible container, sealed on one or both sides by a flexible foil.

In a further embodiment of the invention, the container comprises at least two compartments for substances, wherein the compartments are preferably closed with a breakable seal.

Preferably all parts are molded, wherein preferred materials comprise polypropylene (PP) and/or cyclo-olefine-copolymers (COC). Further materials for molding/producing the package assembly may be of the group of polybutylene terephthalate (PBT), polyphenyle sulfide (PPS), liquid crystal polymers (LCP) including blends and modified types thereof. It is also obvious to use all kinds of polymers like PE, PP, ABS, PC, PA, POM, PS including blends and modified types thereof. Further thermosetting materials may be used, like epoxy molding compounds, melamine formaldehyde molding compounds, melamine phenolic molding compounds (types from Bakelite AG). It is also imaginable to use glass or ceramics, at least for parts of the package. All materials may be filled with pigments for light protection, especially blue light protection, of the substance contained in the package. It is also possible to combine different materials especially for different parts with special functions materials with particularly suitable characteristics can be chosen in order to facilitate more reliable function of the package. Examples for the hinge means are polyolefins or thermoplastic elastomers (SEBS, TPU), the container may consist of COC, PBT or LCP, the breakable seal could be made out of PS or PPS while all other parts are molded from a cheap standard polymer like PP. A preferred embodiment would be a PP Package with COC container, wherein COC provides good barrier properties. In this embodiment the package could be molded by two-shot injection molding.

The container and/or compartments are preferably round (circular or oval), but, if appropriate, also angular (square, rectangular or triangular). The containers have volumes which are adapted to their purpose, so that if used correctly and with a plurality of components to be mixed together, they permit homogeneous mixing. The container may comprise flexible side walls, or flexible separation walls for providing a plurality or compartments. According to some embodiments, the volume of the containers may be variable. The variable volume of the container may be provided by flexible wall constructions or additional movable plunger constructions inserted inside the container for variable adjusting the volume as desired.

Preferably, the base and the lid with the levers comprise a similar shape in projection to the support surface or preferably at least similar dimensions of the levers for providing a stable stand, which prevents tilting when applying a force onto a lever for opening, when the package assembly is standing on a surface. According to another embodiment, the base may further comprise a ring member, to enable a user to wear the package assembly like a ring on one or more fingers.

Preferred dental substances are: dental primers, bondings, etching gel/liquids, filling materials (composites, resign modified glass ionomer cements, temporary filling materials), varnishes. The package assembly may of course comprise other than dental material like glue (e.g. cyanoacrylate), pharmaceuticals (liquids, gels, pastes), varnishes (samples of nail polish, touch up paints), cosmetics (lip gloss), a substance for the treatment or prevention or identification of caries, a substance for the prevention or identification or removal of plaque, a substance for root canal treatment, a substance for the removal of carious or decayed or infected dentine or enamel and/or a substance for the removal of denaturated dentine.

The subject of the invention may also be preferably provided with a kit further comprising at least one of the following members: dental instruments, such as excavators, in particular disposable dental instruments; brushes, particularly of differents sizes and hardnesses; disposable cartridges so that the system can be used as a refillable system; gloves and/or at least any one of the materials mentioned above.

The invention relates also to a method for providing dental substances, which comprises the steps of: providing a package assembly according to any of the previous embodiments, opening the initial closed package assembly by pressing the two levers together, and taking the substance out of the container. If the lid is sealed with a breakable seal to the container, the method comprises before opening the step of pressing the lid in the direction of the container means for breaking the seal. The container may also be closed during using the package assembly by pressing the lid onto the container means.

The present invention will be further described with reference to the claims accompanying drawings exemplifying preferred embodiments of the invention wherein like reference numerals refer to like parts in the several views, and wherein:

FIG. 10 is a top view of a dental package assembly comprising two containers;

FIG. 11 is a view somewhat similar to FIG. 10 except that an additional T-shaped lid is depicted;

FIG. 12 is a perspective view of a dental packaging assembly according to a second aspect of the present invention

FIG. 18 shows a perspective view of a package assembly somewhat similar to FIG. 11 providing two additional applicators attached to the package assembly;

Figure 1:
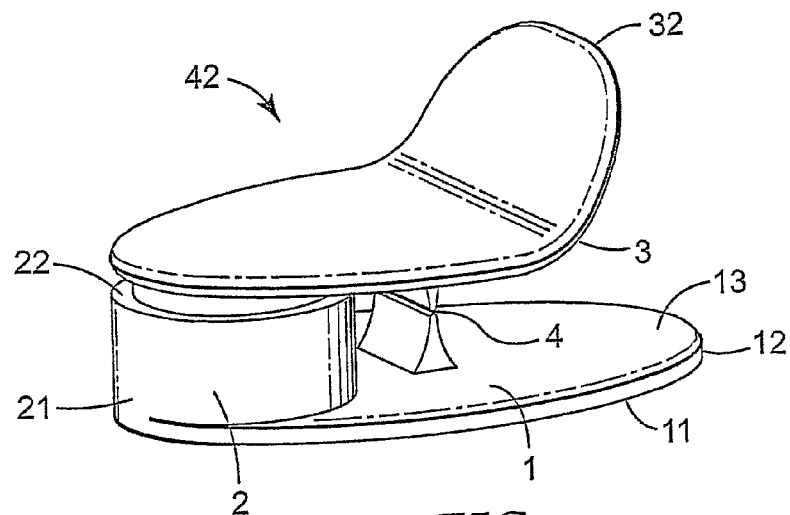
FIG. 1 is a perspective view of a dental packaging assembly according to a first aspect of the present invention.

The package assembly 42 according to a first aspect of the present invention is illustrated in FIGS. 1-6. The package with a container 2 can be made as a one shot part or a molded plastic part, comprising a base 1 with the container 2 for the substance and a lid 3 for closure of the container 2. A hinge 4 connects the lid 3 and the base 1, wherein the hinge 4 could be separate or integrally molded with the lid 3 and the base 1 (a "living hinge"). In this embodiment, the lid 3, the container 2, the base 1, and the hinge 4 are molded integrally.

Figure 2:
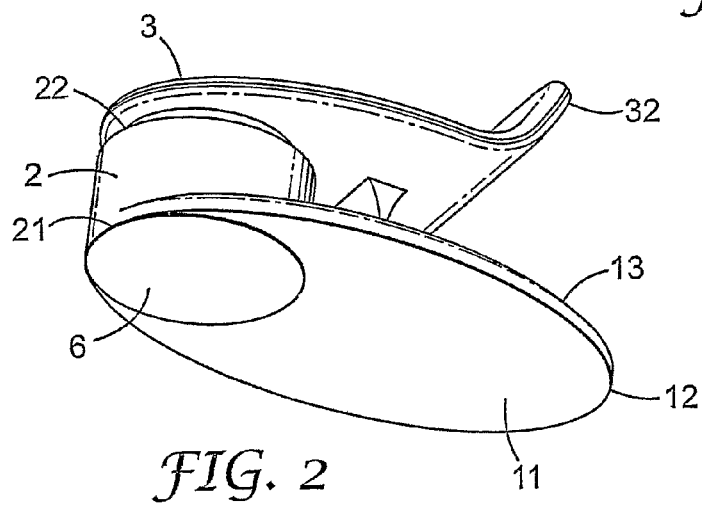
FIG. 2 is another rotated perspective view according to FIG. 1.
Figure 3:
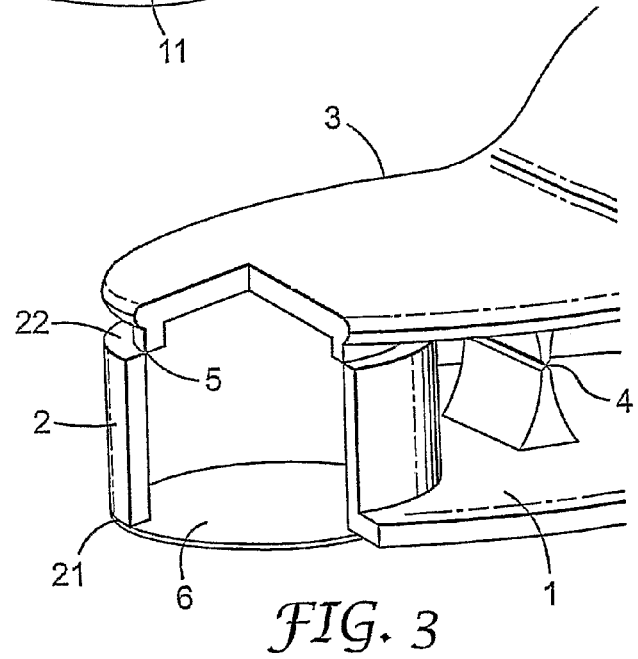
FIG. 3 is an enlarged, partially cross-sectional, view of the container shown in FIG. 1.

Preferably the package assembly comprises after molding a container 2 with a first open opening 21 adjacent to the base 1, whereas a second opening 22 of the container, adjacent to the lid, is closed and conjoined with the lid 3. The interface between the lid 3 and the second opening 22 of the container 2 provides a breakable seal 5 as shown in FIG. 3. After filing the substance into the container 2, the second opening 21 is sealed by a foil or film 6 at the base as shown in FIG. 2. Instead of a foil seal 6 a plug can be used which is mounted via a press fit and/or stuck or fitted into the opening and, optionally, heat sealed, e.g. by thermo sealing, high frequency sealing or the like.

Figure 5:
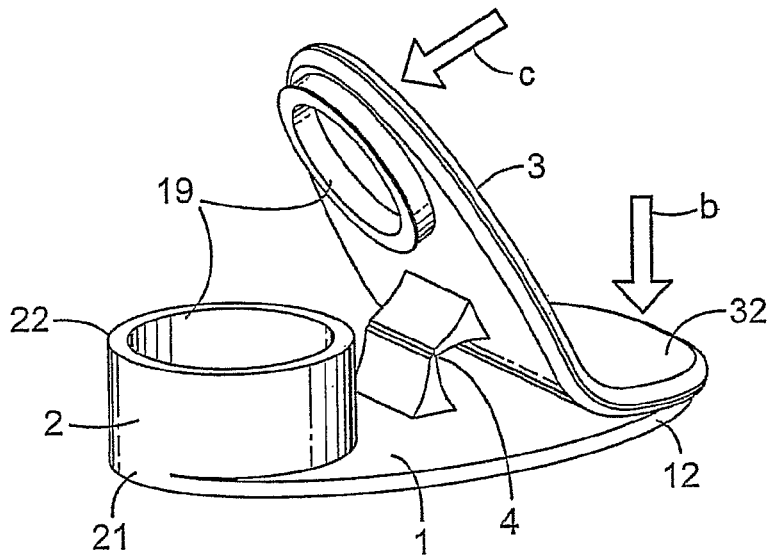
FIG. 5 is a perspective view of a dental packaging assembly according to a first aspect with an open lid position.
Figure 6:
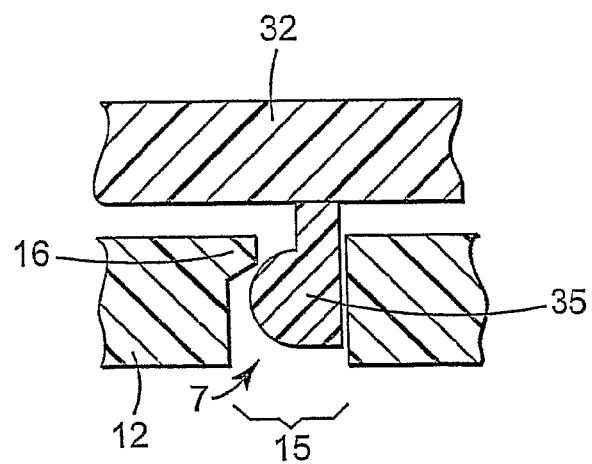
FIG. 6 is an enlarged cross-sectional view of a fixation means.

Preferably, the two levers 32 and 12 are provided on the side of the hinge means and extend essentially in a direction away from the hinge 4. The first lever 12 provides a projection onto the surface for providing a tilt resistance base. This embodiment is advantageous since the tilt resistance is still warranted when a force for opening the package assembly is applied on lever 32 in the direction of arrow b) in FIG. 5. Preferably the first lever 12 is essentially flat on its downside, for providing a planar support with the underlying surface. The second lever 32 is preferably bent upwardly in a direction away from the base 1. This is advantageous for an easy opening of the package assembly, wherein in addition the bent portion of the lever 32 provides a surface for essentially planar contact with the base 12 in an open state of the package assembly, as can be seen in FIG. 5. The planar contact between the two levers facilitates applying a fixation mechanism as discussed below. Preferably, lever 32 at the lid 3 is designed to provide appropriate leverage for easy, single-hand opening of the package assembly. The lever 12 at the base 1 is preferably designed to provide a sufficient opposing force to the downward force imposed by the lid lever 32 during opening, to maintain the package assembly in a more or less stable position on the work surface (e.g., dental tray). The lever at the base preferably also provides a support for the opened package assembly on the work surface to keep it from tipping or moving around the work surface during use.

Figure 4:
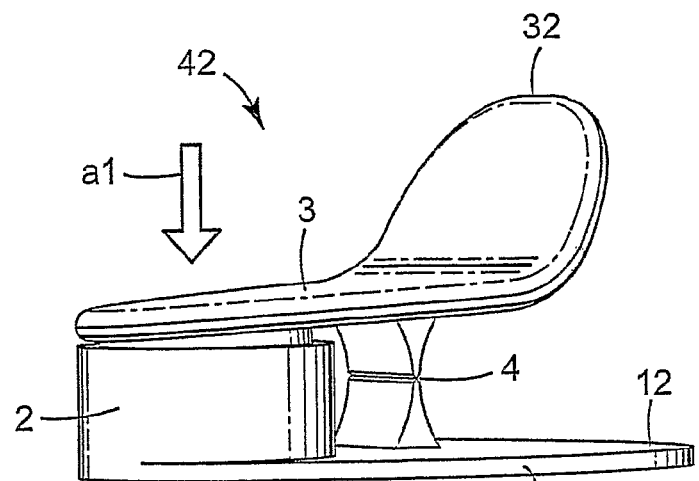
FIG. 4 is a view somewhat similar to FIG. 1 except that the position of the lid during the activation step is illustrated.

According to another embodiment of the present invention, the base 1 with the container 2 may be sealed integrally and the lid 3 may be produced separately. The lid may be connected to the base via a hinge, like a pivot. The lid 3 can close the second opening at the second end 22. The lid 3 preferably provides an airtight seal at the second opening 22 which can indicate tamper resistance and the interface between the container 2 and the lid 3, such seal can be achieved by providing a breakable seal 5, such as that depicted in FIG. 3. Upon pushing on the lid 3 in the direction indicated by the arrow a1)

shown in FIG. 4, the breakable seal 5 can be ruptured. To open the container the lever 32 can be pushed in the direction of the base 1 as shown by arrow b) in FIG. 5.

Figure 14:
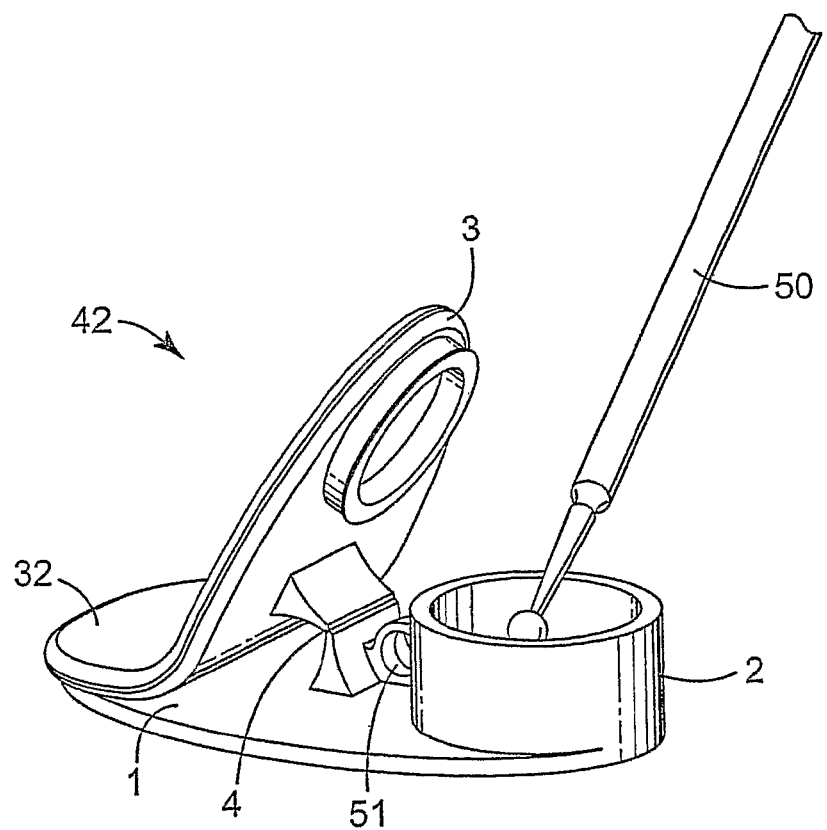
FIG. 14 shows the package assembly according to FIG. 13 with an applicator in use.

Opening and closing the package assembly can be done with one hand or one finger. After the container has been opened, the substance can be taken out with an instrument, preferably with a brush or an applicator 50 as depicted in FIG. 14. The assembly can function as a dosing unit for dispensing and applying amounts of substance predetermined by the volume of the container. The container may also comprise marks for measurement the amount of the substance like a measuring cup.

Figure 22A:
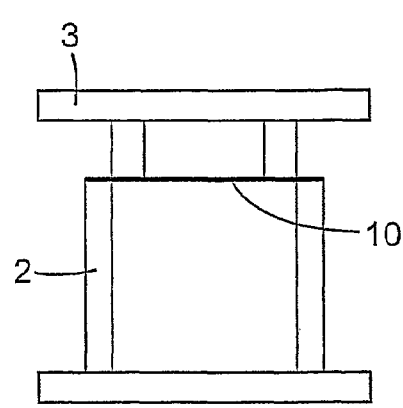
FIG. 22a to 22c show a package assembly with a container sealed upon with a foil.
Figure 23A:
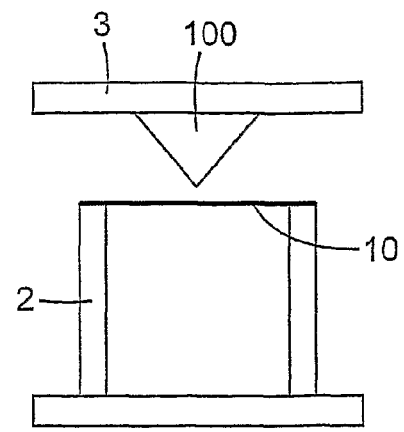
FIG. 23a to 23b show a package assembly according to another embodiment with a container sealed upon with a foil.
Figure 22B:
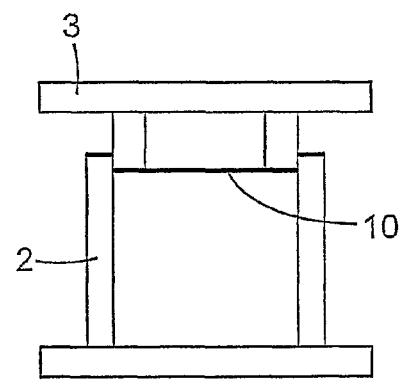
Figure 23B:
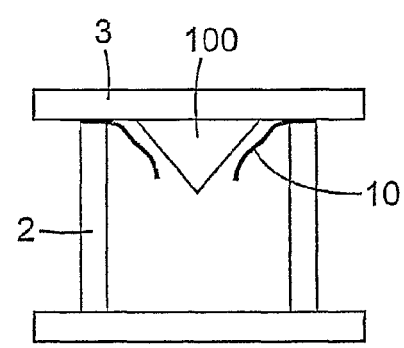
Figure 22C:
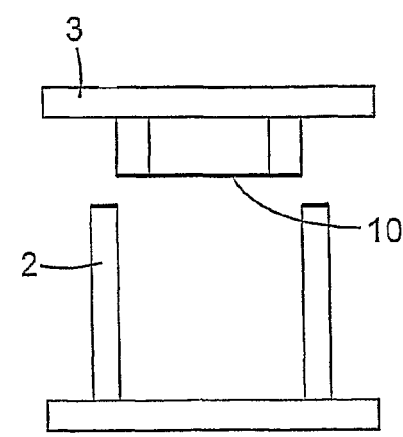

The breakable seal 5 as shown in FIG. 3 preferably provides besides an airtight sealing also a tamper-evident resistance which indicates an intact and new unused package assembly. This can preferably be achieved by using a foil 10 which is sealed upon the container, as shown in FIGS. 22a to 22c and 23a and 23b. The foil 10 is pierced or punched by a spike 100 or cutting edge respectively as shown in FIGS. 23a and 23b. Within another embodiment, as shown in FIGS. 22a to 22c, the foil 10 is also attached to the lid 3 to ensure the foil 10 is removed from the container 2 when the package is opened (FIG. 22c) and the lid stays close during transport of the package. Alternatively the foil 10 can have a breaking line which facilitates easy rupturing during activation of the package.

By means of the package assembly according to the invention, it is possible, in particular, to safely store substances which are sensitive to air or light.

To permit the lid to stay in the open position (as depicted in FIG. 5), a fixation system or mechanism 7 can be integrated in the base or the lid, and is preferably located at the end of the lever and 32 the base 12. To apply a fixation between the lever 32 and the lever 12, the lever 32 may be pushed in the direction shown by arrow b) in FIG. 5. A fixation mechanism with a snap fit or press fit can be provided by providing a recess 15 in the base 1 and a protrusion 35 at the lid 3. The protrusion 35 provides engagement with the recess 15 behind the rim 16. The fixation mechanism 7 is preferably releasable so that the package assembly can be reclosed. To remove the lever 32 from lever 12, the lever 32 is lifted away, e.g. pivoted upwards. Alternatively, fork-like webs can be used instead of the recess 15. The location of the snapper 35 and recess or fork-like webs can also be inversed. In other words, the clip 35 can be provided at the base 1 and the recess 15 or fork-like webs can be provided on the lid 3. Further options for the fixation mechanism 7 include the use of repositionable adhesives, mechanical fasteners and other frictional retainer or retention means.

To reclose the package assembly, the lid 3 can be pushed in the direction shown by arrow c) in FIG. 5 back on the container 2. Due to the strain of the material at the breakable seal 5 caused during activation (indicated by arrow a1 in FIG. 4) a flexible, locking appendage 19 is created which will provide a friction fit between the lid 3 and the end 22 of the container when the lid 3 is pushed onto the container 2.

To keep the package assembly 1 fixed on a work surface, the lower side 11 of the base 1 may be sticky, e.g., coated with glue or a pressure sensitive adhesive. It is also possible to use soft, elastomeric material for part or all of the base 1. Such a base could be manufactured by a two shot injection molding process. Further options are providing the lower side of the base 11 with suction cups, microreplicated surfaces which increase the friction between the assembly and the work surface, magnets surface, mechanical fasteners or the like. In a particular embodiment, the foil seal 6 can have an adherent surface, which makes injection molding of the part easier.

Figure 7:
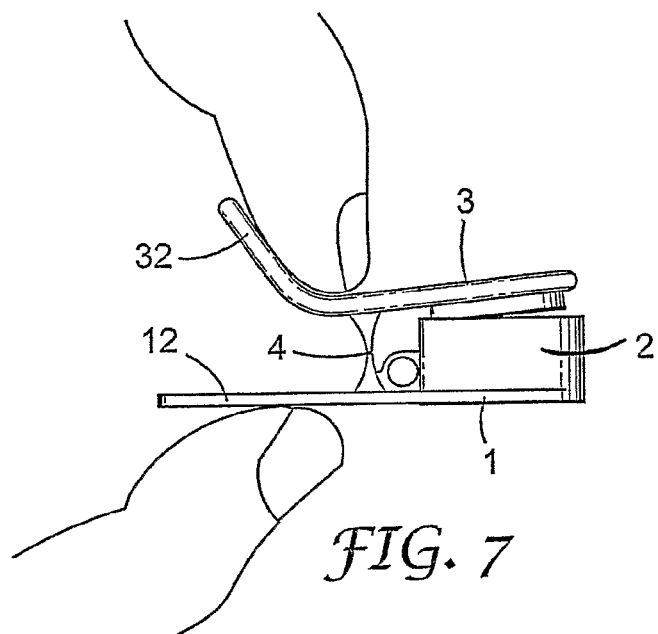
FIG. 7 is a photographical side view of a dental package assembly according to a first aspect of the present invention.

FIG. 7 is a photographical side view illustrating a preferred size of a dental package assembly according to the present invention. There are at least two preferred methods for opening a closed package assembly. According to a first method, a user holds the package assembly between two fingers, like depicted in FIG. 7, and pushes with the two fingers the two levers 32 and 12 together, which results in opening the lid 3 from the container 2. The open package assembly may afterwards be placed with the base 1 on a surface. In one preferred embodiment, the base 1 may further comprise a ring member, to enable a user wearing the package assembly like a ring on one or more fingers. Another method for opening the closed package assembly comprises the steps of placing the package assembly with the base 1 on a supporting surface and pressing with one hand, preferably with one finger on the lever 32 resulting in a pivoting movement of the lid 3 and opening the container 2.

Figure 8:
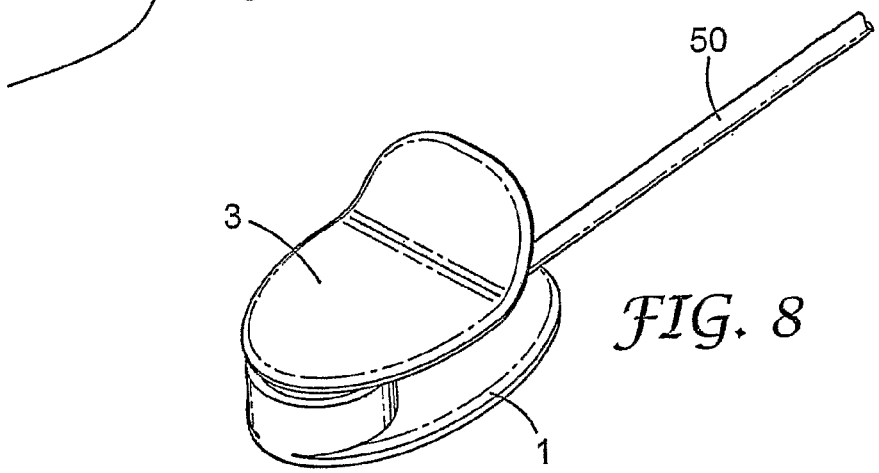
FIG. 8 is a photographical top view of a denial package assembly comprising a dental brush.
Figure 9:
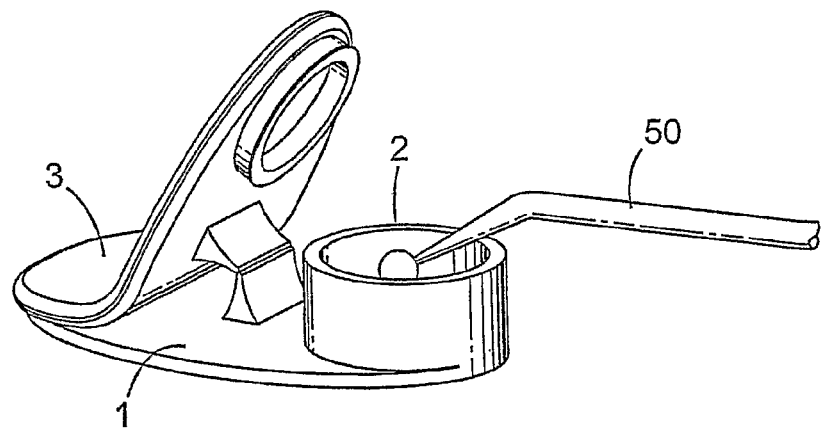
FIG. 9 is a photographical top view of a dental package assembly with the lid in an open position and a dental brush.
Figure 13:
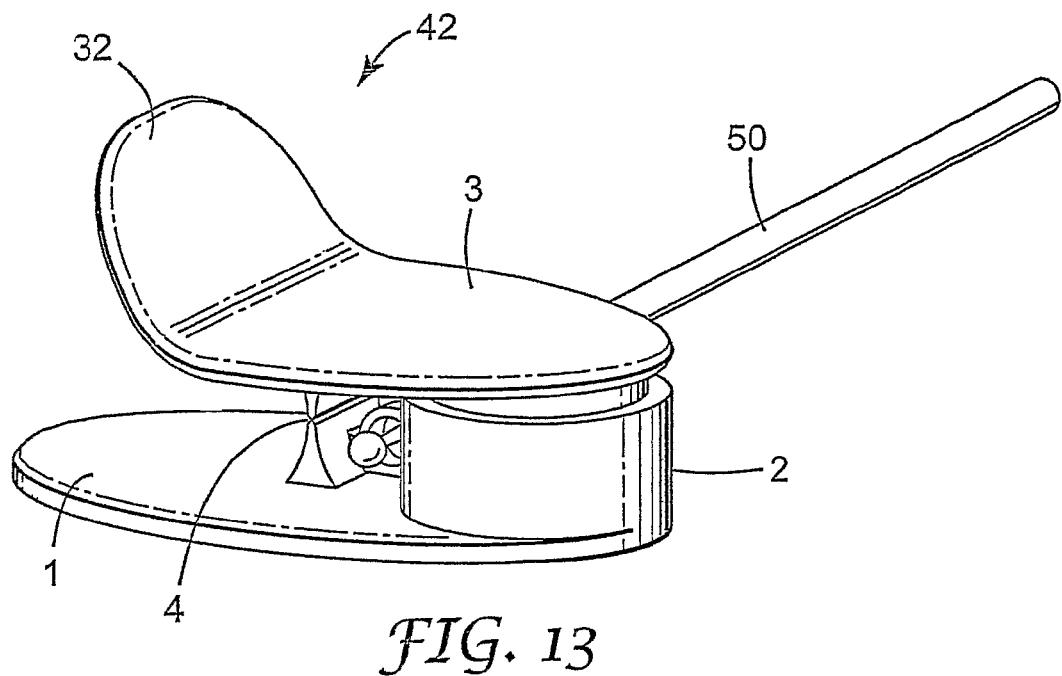
FIG. 13 shows a package assembly somewhat similar to FIG. 1 but providing an additional applicator attached to the package assembly.
Figure 15:
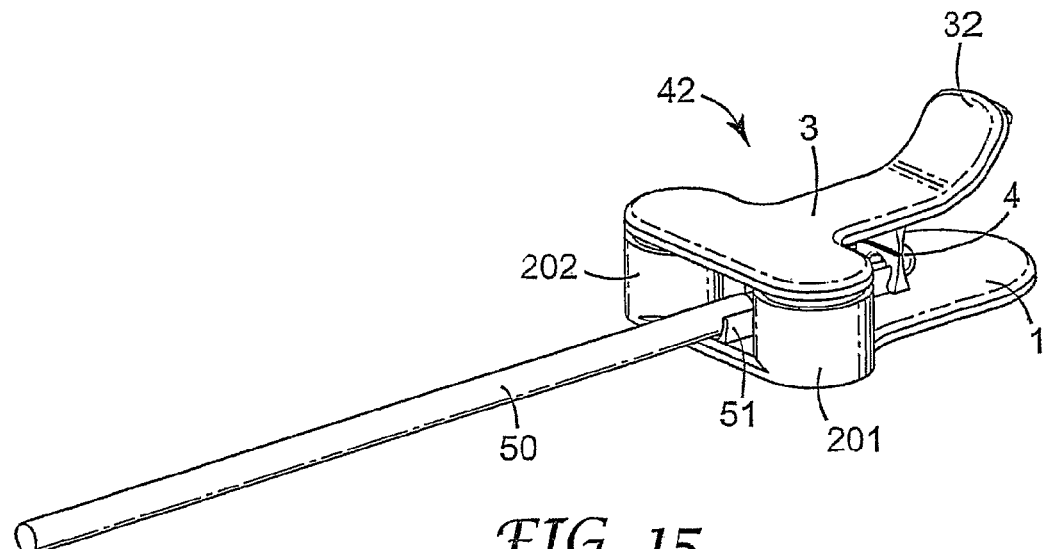
FIG. 15 shows a perspective view of a package assembly somewhat similar to FIG. 11 providing an additional applicator attached to the package assembly.
Figure 16:
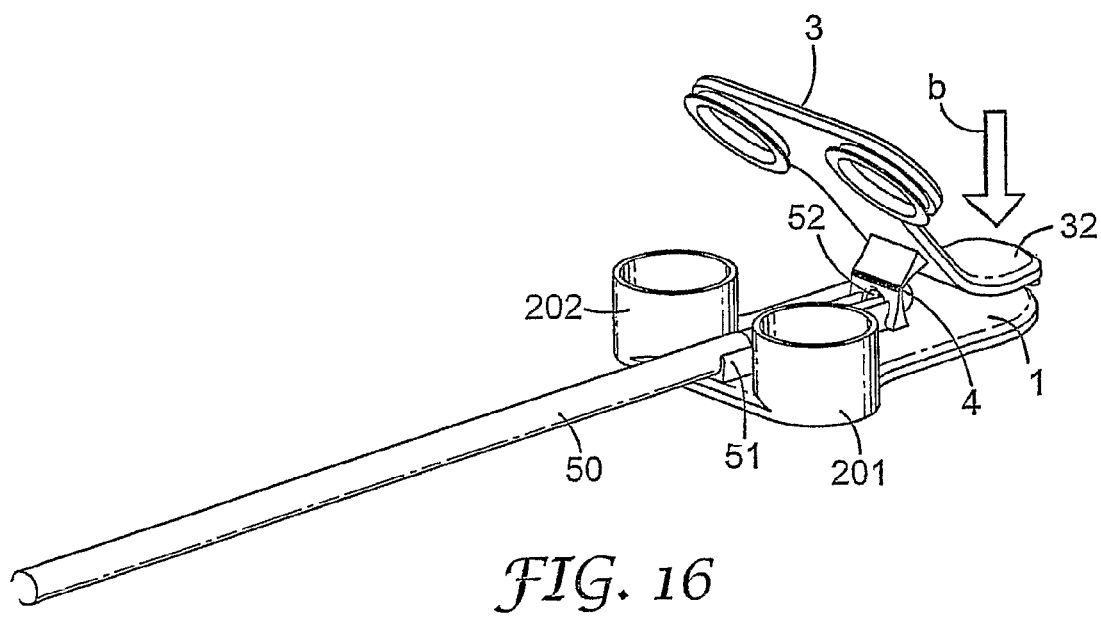
FIG. 16 shows the package assembly according to FIG. 15 with an open lid.
Figure 17:
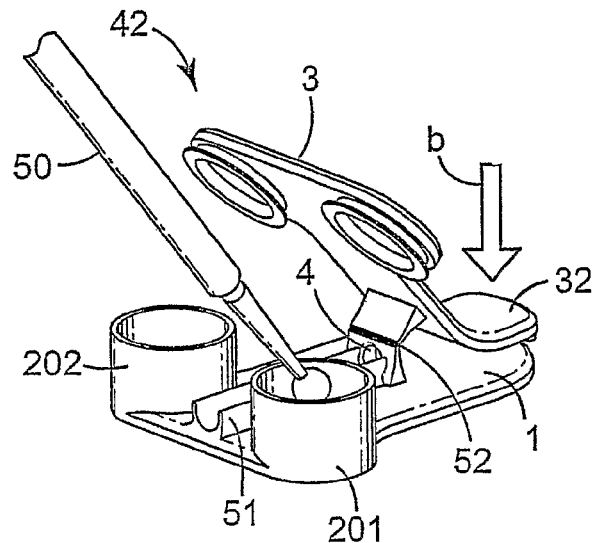
FIG. 17 and FIG. 18 show the package assembly according to FIG. 15 and FIG. 16 with an applicator in use.
Figure 18:
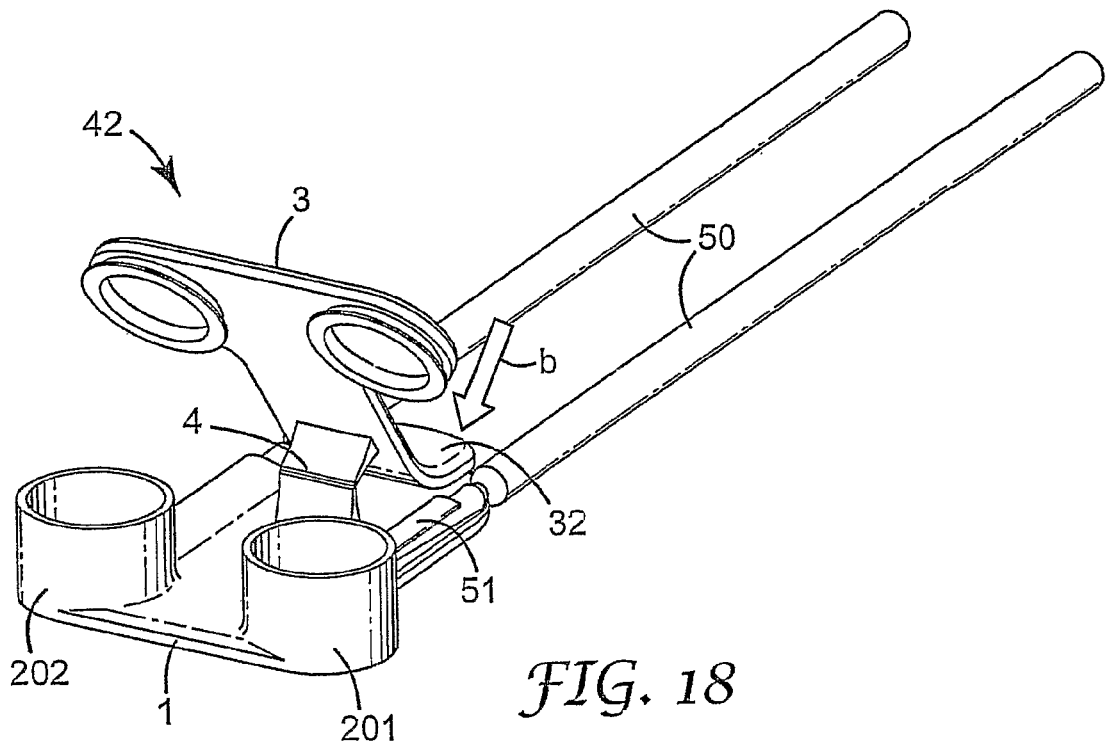
Figure 19:
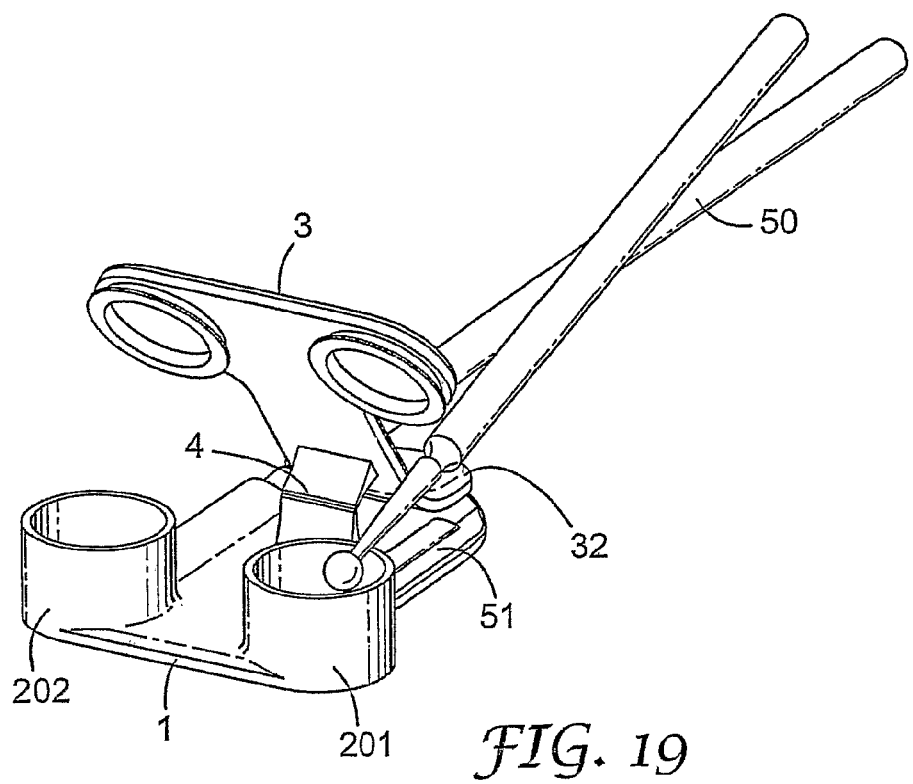
FIG. 19 shows the package assembly according to FIG. 19 with one of the applicators in use.
Figure 20:
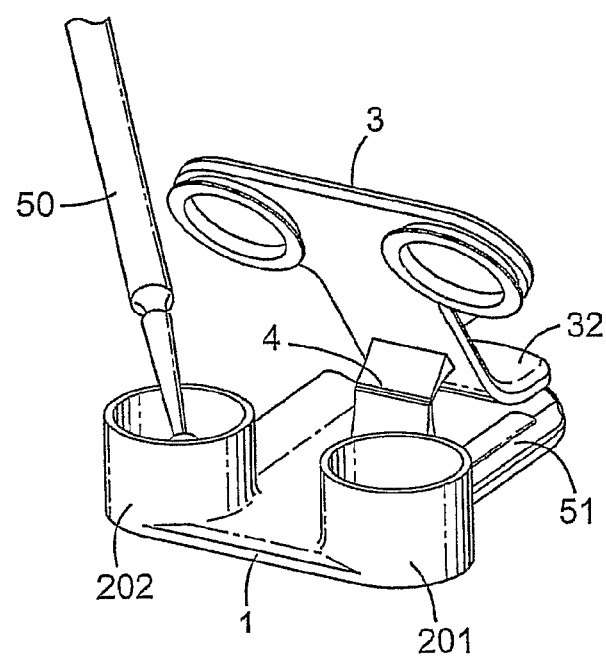
FIG. 20 shows the package assembly according to FIGS. 18 and 19 with the second applicator in use.

FIG. 8 is a photographical top view of a dental package assembly comprising an applicator 50 attached from behind. FIG. 9 is a photographical top view of a dental package assembly with the lid in an open position and an applicator 50 in use. If the dental treatment is made via a brush the package may include one or more standard disposable brush like a micro brush or other dental application tools 50 as shown in the photographical FIGS. 8 and 9 or in FIGS. 13, 15 and 19. The applicator 50 may be fixed at the package by some mechanism like a snap lock or a clamp 51. The applicator 50 may be arranged laterally to the package assembly as depicted in FIG. 13, from behind like in FIGS. 8, 19 and 20 or from ahead as shown in FIGS. 15 and 16. If the applicator 50 is arranged from ahead or from behind, the clamp 51 may be arranged adjacent to the hinge 4 as shown in FIG. 18 to 20 or in projection with the hinge 4 as shown in FIG. 15 to 17. The hinge may provide a cut-out 52 for inserting the applicator which will provide further stability.

According to another aspect of the invention, the package assembly is designed for storage of two- or multi-component substances. Different arrangements of two containers 201 and 202 with components A and B are shown in FIG. 10, 11 and FIG. 15 to 20. In the design of FIG. 10a to 10c, two containers 201 and 202 are arranged on the base 1 adjacent to each other. In another embodiment shown in FIG. 10d the containers 201 and 202 can share a common wall 203, in the third embodiment in FIG. 10e, the containers 201 and 202 are concentrically located. Each container can have separate lids for independent opening and closing the two substances. Preferably for easy single-hand handling, the package assembly comprises a single lid 3 that covers both containers 201 and 202, as shown in FIG. 15 to 20. The lid can be configured in various shapes to provide coverage of the multiple containers. For example, a T-shaped lid, like that shown in FIG. 11 and FIG. 15 to 20, can be used. Pressing sequentially on the portion of the lid above the containers 201 and 202 can sequentially activate the two containers.

The base may further comprise an area or a well, inside the container or in addition adjacent to the container that can be used for intermediate holding a substance into which a brush or tool can be dipped. In case the mixing well is part of the container, the well is re-closable by the lid which would be desirable for instance for light protection.

Figure 21A:
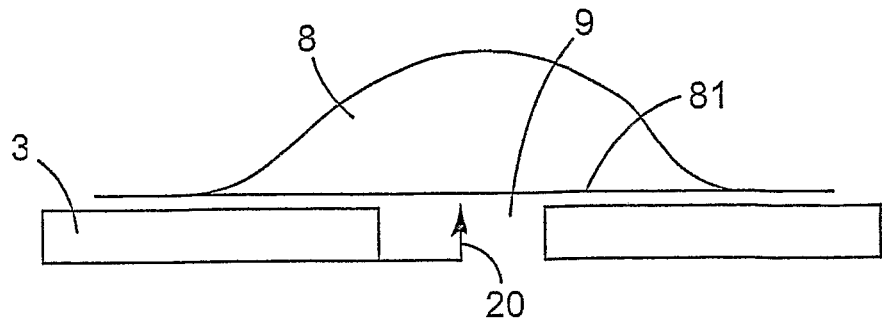
FIG. 21a to 21c show an arrangement to facilitate an unerring rupture of the base foil of a sachet.
Figure 21B:
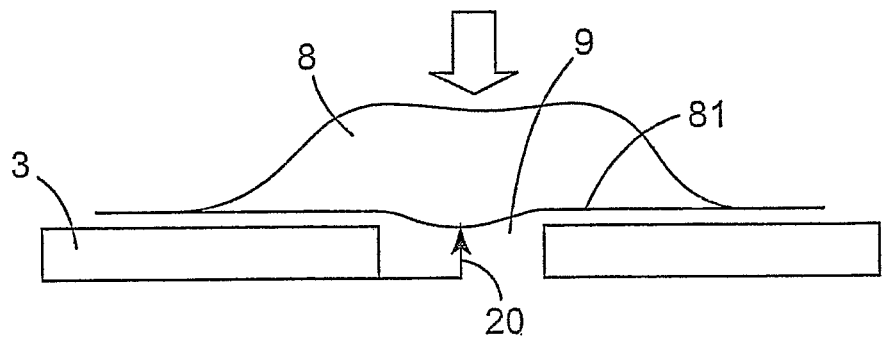
Figure 21C:
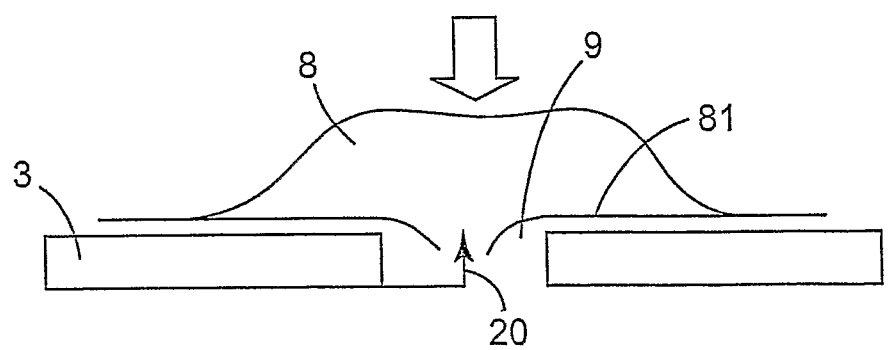

FIG. 12 shows a further embodiment of the present invention, wherein instead of arranging multiple containers on the base a first component of the substance 23 may be stored inside a single container 2. The container preferably has a volume which is suitable for receiving the total amount of substance which is to be mixed or has been mixed. A second component 24 could be stored within a foil sachet 8, which is arranged on top of the lid 3. The lid 3 comprises a bore 9, which is sealed by a base foil 81 of the sachet 8. Preferably a sealed sachet 8 attached with the base foil 81 to the lid 3 above the bore 9. The sealing of the sachet 8 can be done by first sealing a base foil 81 onto the lid 3 (whole surface or ring). Thereon, a deep drawn part of a sachet 8 provides an upper opening, wherein the deep drawn part is filled with a component. The sachet is heron sealed with the base foil 81, which is already attached to the lid 3, by providing the whole assembly arranged upside down on top on the upper opening of the deep drawn part of the sachet 8. An alternative solution for sealing can be done by pre-manufacturing the sachet 8, comprising a base foil 81, and sealing it onto the lid 3 at the opposite side to the container 2 above the bore 9. The base foil may be larger than the deep drawn part of the sachet and extend over the shape of the deep drawn foil. In this case the deep drawn part and the base foil are sealed along an inner ring (two foils are sealed to each other) and the sachet is sealed to the lid along an outer ring at the extended part of the base foil only (only base foil is sealed to the lid). This provides the advantage that sealing of the sachet to the lid requires sealing through one foil only instead of two. For a predetermined rupture of the base foil 81 at the position of the bore 9, the sachet may provide a predetermined breaking point. According to another embodiment, there is a little spike 20. The spike 20 is preferably arranged between the sachet 8 and the lid, e. g. in the bore 9 as depicted in FIG. 21a to FIG. 21c. Alternatively the spike 20 may be arranged within the sachet 8 in the deep drawn part of the sachet 8 to facilitate an unerring rupture of the base foil 81 at the portion above the bore 9, upon pushing onto the sachet 8, in the direction shown by the arrows in FIG. 21, for activation. Instead of a spike a cutting edge may be used e. g. along the edge of the bore or partially arranged on the edge of the bore or next to it.

Upon activation the package assembly by pressing onto the sachet 8, the base foil 81 of the sachet will rupture at the bore 9 and the component 24 of the substance will flow into the container 2 and optionally contacting a component stored in the container 2. Preferably, this embodiment of the present invention also comprises a breakable seal 5, which at the same time or sequentially during activation, will break thus opening the package assembly.

The breakable seal could be arranged directly on the base surface. The surface 13 of the base can be used for mixing of the components like on a pad. Optionally, the base 1 could be made with a much larger size to facilitate mixing or it could be extended for instance by a (e.g. paper or plastic film) mixing pad. This design could especially be used for powder/liquid substances wherein the powder is preferably stored in the container and the liquid in sachet 8.

FIG. 13 shows a package assembly according to a first embodiment of the present invention with an additional applicator 50 attached laterally to the base 1 by a clamp 51. FIG. 14 shows the package assembly according to FIG. 13 with the applicator in use for dispensing the substance of container 2.

The FIGS. 15 to 20 show package according to another preferred embodiment, which comprises two containers 2. The FIGS. 15 to 17 illustrate the working steps of using a package assembly of the present invention with two containers and one applicator. FIG. 15 shows the prefilled package assembly 42 with two containers 201 and 202 with the base 1 and the lid 3. The base 1 and the lid 3 are connected with a living hinge 4, which comprises a cut-out 52 for incorporating an end of an applicator 50 which is fixed to the base 1 by a clamp 51. The two containers 201 and 202 are opened simultaneously by pushing onto the lever 32 in the direction shown by arrow b) in FIG. 16. The working step of mixing, stirring or dispensing the component of container 201 with an applicator 50 is illustrated in FIG. 17.

FIGS. 18 to 20 show a package assembly similar to FIG. 15 but with two applicators 50 attached with clamps 51 sidewise to the base 1 from behind. Due to the sidewise arrangement of the applicators 50, the living hinge 40 does not comprise a cut out as in the above described embodiment. To open the package assembly, the lid 3 can be pushed in the direction shown by arrow b) in FIG. 18, wherein applicators 50 provide an additional steadiness, since they extend into the backward direction of the package assembly.

For swabbing a brush or mixing the components with a brush, a further area or cavity may be provided located at the base, e.g. between the compartments 201 and 202 in FIG. 18 or as part of the container that can be reclosed by the lid.

Preferred materials for the molded parts can be e.g. polypropylene (PP) and/or cyclo-olefine-copolymers (COC). For a transparent appearance of the package an orange coloring can be used, for filter blue light and protecting the substance or the compartments from specific light wavelength.

Also features shown in the attached drawings either alone or in any combination with other features and not explicitly mentioned in the description do belong to the present invention, either alone or in combination with any other feature(s) described or shown herein.

Moreover, the present invention is realized by the features of the claims and any obvious modifications thereof. It is in no way intended to limit the scope or spirit of the invention as described above or set out in the claims.

The invention claimed is:

1. A package assembly for placement on a surface and for storing and/or delivering substances such as dental substances, comprising:
   a) at least one container comprising a base and a lid; and
   b) at least one hinge connecting the base and the lid;
   wherein the base and the lid comprise first and second levers, and the container can be opened by moving the first and second levers towards each other;
   and wherein the container contains at least one dental substance and is sealed with a breakable tamper-evident seal.

2. The package assembly according to claim 1, wherein the hinge is provided between the first and second lever.

3. The package assembly according to claim 1, wherein the container is adapted for air-tight closing of the container with the seal.

4. The package assembly according to claim 1, wherein an end of the second lever is bent in a direction away from the first lever.

5. The package assembly according to claim 1, wherein the base, the lid and the hinge are integrally molded.

6. The package assembly according to claim 1, wherein the base and/or the lid are manufactured with an opening for filling the container after manufacturing and for sealing with a seal.

7. The package assembly according to claim 6, wherein the container is sealed with a seal at a first end.

8. The package assembly according to claim 7, wherein the seal is a foil, a plug, or part of the base.

9. The package assembly according to claim 7, wherein the seal is a foil, a plug, or part of the lid.

10. The package assembly according to claim 1, wherein a back surface of the base comprises a non-skid and/or sticky layer for standing the package assembly on a surface.

11. The package assembly according to claim 1, wherein the assembly further includes a ring member, to enable a user to wear the package assembly like a ring on at least one finger.

12. The package assembly according to claim 1, wherein at least a back surface of the base comprises a soft elastic material.

13. The package assembly according to claim 1, wherein the first or second levers comprise a fixation mechanism for attaching the second lever to the first lever and to ensure that the lid stays open after having been opened.

14. The package assembly according to claim 13, wherein the fixation mechanism comprises a recess and a clip device for releasably engaging the clip with the recess.

15. The package assembly according to claim 13, wherein the fixation mechanism comprises a fork at one lever and a snapper at the second lever for releasably engaging said snapper with the fork.

16. The package assembly according to claim 13, wherein the fixation mechanism comprises sticky glue or pressure sensitive adhesive for attaching the first and second levers together.

17. The package assembly according to claim 1, wherein the package comprises a disposable applicator.

18. The package assembly according claim 1, wherein the assembly comprises at least two containers.

19. The package assembly according to claim 18, wherein the at least two containers are provided separately with independent openings.

20. The package assembly according to claim 18, wherein the at least two containers comprise one common lid.

21. The package assembly according to claim 20, wherein the common lid is T-shaped, and the two containers are arranged side by side.

22. The package assembly according to claim 1, further comprising an area adapted for swabbing a brush or a mixing cavity for mixing components with a brush.

23. The package assembly according to claim 22, wherein the mixing cavity is part of the container and is re-closable by the lid.

24. The package assembly according to claim 1, wherein the lid comprises a second container adapted for storing a substance.

25. The package assembly according to claim 24, wherein the second container and/or the lid comprises a bore adapted for connecting the container with the second container of the lid for dispensing the substance into the container.

26. The package assembly according to claim 25, wherein upon activation the base foil of the sachet will rupture at the bore for dispensing the additional substance into the container.

27. The package assembly according to claim 1, wherein the package assembly exhibits an orange color, to filter blue light.

28. The package assembly according to claim 1, wherein the container is sealed with a foil.

29. The package assembly according to claim 1, wherein the lid or container comprise a self-cleaning or low energy surface.

30. The assembly according to claim 1, wherein the substance comprises at least one of the materials selected from the group consisting of: dental primers; bondings; etching gel/liquids; filling materials, such as composites, resign modified glass ionomer cements; temporary filling material; varnishes; glue, such as cyanoacrylate; pharmaceuticals, such as liquids, gels, pastes; varnishes; nail polish; touch up paints; cosmetics, such as lip gloss; a substance for the treatment or prevention or identification of caries; a substance for the prevention or identification or removal of plaque; a substance for root canal treatment; a substance for the removal of carious or decayed or infected dentine or enamel and/or a substance for the removal of denaturated dentine.

31. The package assembly according to claim 1, wherein the breakable seal can be broken by pushing the lid in a direction substantially towards the container.

32. The package assembly according to claim 1, wherein an appendage is created at the breakable seal during activation and provides a friction fit between the lid and second end of the container when the lid is pushed onto the container.

33. A method for providing dental substances, comprising the steps of:
a) providing a package assembly comprising at least one container comprising a base and a lid and at least one hinge connecting the base and the lid, wherein the base and the lid comprise first and second levers, and wherein the container can be opened by moving the first and second levers towards each other, and wherein the container contains at least one dental substance and is sealed with a breakable tamper-evident seal, and
b) opening the package assembly by pressing the two levers together.

34. A method for providing dental substances according to claim 33, comprising before step b) the further step:
a1) pressing the lid in substantially the direction of the container for breaking the seal.

35. A method for providing dental substances according to claim 33, comprising after step b) the further step:
c) closing the container by pressing the lid onto the container.

* * * * *

UNITED STATES PATENT AND TRADEMARK OFFICE
CERTIFICATE OF CORRECTION

PATENT NO.         : 8,794,433 B2
APPLICATION NO.    : 10/598994
DATED              : August 5, 2014
INVENTOR(S)        : Marc Peuker et al.

It is certified that error appears in the above-identified patent and that said Letters Patent is hereby corrected as shown below:

On the Title Page, Column 2, Item (57) (Abstract)
Line 13                     Delete "towards to" and insert -- towards --, therefor.

In the Specification

Column 1
Line 22                     Delete "computes." and insert -- compules. --, therefor.

Column 3
Line 47                     Delete "gloss," and insert -- gloss; --, therefor.

Column 6
Lines 14-15                 Delete "cyclo-olefine-copolymers" and insert
                            -- cyclo-olefin-copolymers --, therefor.
Line 17                     Delete "polyphenyle" and insert -- polyphenylene --, therefor.

Column 7
Line 12                     Delete "differents" and insert -- different --, therefor.
Line 52                     Delete "invention" and insert -- invention; --, therefor.

Column 8
Line 4                      Delete "use," and insert -- use; --, therefor.

Column 11
Line 27                     Delete "e. g." and insert -- e.g. --, therefor.
Line 33                     Delete "e. g." and insert -- e.g. --, therefor.

Signed and Sealed this
Twelfth Day of May, 2015

Michelle K. Lee
*Director of the United States Patent and Trademark Office*

CERTIFICATE OF CORRECTION (continued)
U.S. Pat. No. 8,794,433 B2

Column 12

Line 17                         Delete "cyclo-olefine-copolymers" and insert -- cyclo-olefin-copolymers --, therefor.